Figure 1:
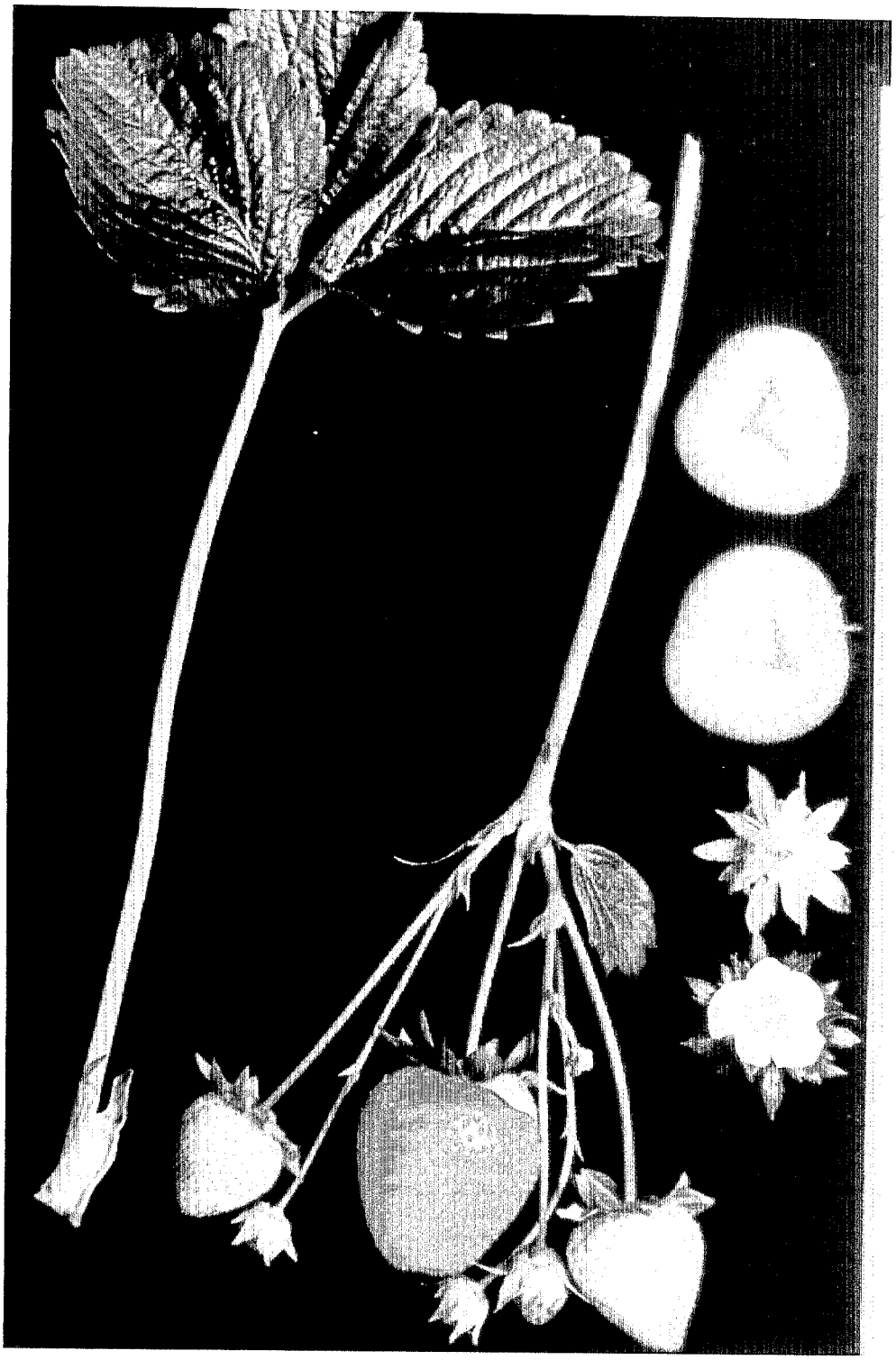

United States Patent [19]

Johnson, Jr.

[11] Plant 4,763

[45] Sep. 1, 1981

[54] STRAWBERRY PLANT

[75] Inventor: Harold A. Johnson, Jr., Watsonville, Calif.

[73] Assignee: Driscoll Strawberry Associates Inc., Watsonville, Calif.

[21] Appl. No.: 153,392

[22] Filed: May 27, 1980

[51] Int. Cl.[3] ..... A01H 5/03

[52] U.S. Cl. ..... Plt./49

[58] Field of Search ..... Plt./49

*Primary Examiner*—Robert E. Bagwill

*Attorney, Agent, or Firm*—Townsend & Townsend

[57] ABSTRACT

A new and distinct ever-bearing variety of strawberry plant characterized by its vigorous plant growth and heavy crops when planted in December. The variety is a prolific runner and is further characterized by its showy long, abundant inflorescence and large amount of pollen, and its reddish-brown pedicels. The fruit is smooth and firm with exerted seeds and rounded at the apex, and has a mild, pleasant aroma and high dessert quality.

1 Drawing Figure

This invention relates to a new and distinct variety of strawberry plant which is the result of a cross of the Driscoll patented everbearing variety U.S. Plant Pat. No. 3,274 and Driscoll springbearing selection G8.

The seedlings resulting from the aforementioned cross were grown and asexually multiplied in Shasta County, Calif., and tested in the fruiting beds on the property of growers on the Driscoll Strawberry Associates, Inc. Clones of the seedlings were also held at the Propagation Nursery in Shasta County. One plant was selected from the aforementioned group of seedlings and further asexually reproduced by runners in the Shasta County nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

In the drawing:

FIG. 1 illustrates plant parts of the new everbearing variety which are typical in size, shape and color.

Referring to FIG. 1, a berry is shown in cross-section illustrating the flesh color and characteristic core cavity. The inflorescence shown in the drawing is illustrative of typical branching and relative size during the middle of July. The large inflorescence has pedicels that are reddish green in color with the pedicel holding the primary berry originating from the axil formed by the two peduncles. Also illustrated are the two secondary berries which are often an equal distance from the axil giving the total inflorescence a symmetric outline.

Three secondary peduncles instead of two are not uncommon. The leaf illustrated is typical in size, shape and color but bracts not shown may be present on some petioles. As the season progresses, the peduncles and pedicels lengthen.

The plant of this novel variety is medium in size and considered vigorous for an everbearer. If given ample chilling, it produces heaviest when planted during late December or January, but will crop commercially if planted in March. It is adapted mainly to the central coast region of California. If planted during January, its peak production and largest fruit size comes during July. It will continue producing during September but its fruit size drops significantly after July. Some of its distinguishing characteristics are its showy long inflorescence, firm fruit with exerted seed and good flavor.

The plant is slightly smaller with leaves that are darker but smaller and more rugose than the Driscoll patented Heidi variety, U.S. Plant Pat. No. 3,123. Heidi is a spring fruiting variety, but the two varieties have a similar cropping pattern if the Heidi is given its correct chilling for high production. Both varieties have crown crop fruit of equal size, but the Heidi maintains a superior size during the main crop, especially after the peak production in July.

The new variety has a more visible inflorescence above the plant with reddish pedicels also distinguishing it from the Heidi. Both the flesh and skin of the new variety are considered firm, equal to that of Heidi. It holds its seed in a more exerted position on the fruit than does Heidi. It is prone, as is Heidi, to bronzing after thrip feeding and will crack easily after a rain or after some insecticide sprays. It is more prone to show albino fruit than is Heidi (when areas of the fruit surface between the seed do not color normally and often become puffy and weak, the condition is referred to as albinism). Low carbohydrates within the plants help induce this condition and low carbohydrates may be caused by high nitrogen available to the plant or lack of sunlight.

The new variety is similar to Heidi in that its fruit surface is quite smooth, lacking in longitudinal furrows or other malformed fruit surface conditions. It may have some folded seeded tips on primaries of its main crop, but in general it does not have as many white tips as Heidi. It tends to be more rounded at the apex and not as conic as Heidi if large numbers of fruit are compared. When observing full crate amounts of the fruit picked with the same degree of ripeness, the new variety is darker in color.

The calyx of the new variety is large and showy, but not as large as the Heidi. It is more reflexed than Heidi. Individual sepals may be serrated, but not as prevalent as Heidi and sepals do not overlap as consistently as Heidi. The new variety often produces a white area around and under the calyx, a condition not common to Heidi. Both Heidi and the new variety produce flowers with anthers that produce an abundance of pollen even early in the spring during the flowering of the crown crop.

Even though an everbearer, the new variety is a more abundant runner producer than Heidi at the nursery, as well as the fruiting bed. The dessert quality of the new variety is equal to that of Heidi. The new variety has a mild but pleasant strawberry odor similar to that of Heidi. The new variety has the same degree of susceptibility to injury from the two-spotted mite. The new variety is not as susceptible to mildew as Heidi. It has not been completely tested against the Verticillium or the Red Stele diseases. As a seedling and selection, this variety withstood the natural invasions of certain virus components found in central California without losing its ability to produce.

The new varietal characteristics of the novel plant, described below in detail, were observed mainly during the first fruiting season. Observations were made during July and August in the Watsonville area of California which is a cool coastal area near the Pacific Ocean. The color terminology is in accordance with the Munsell Color System.

Plants: Medium to large, vigorous if given ample chilling before being planted, and has an extensive root system. Isozymes in Leaf Extracts. Phosphoglucoisomerase (PGI): similar to Heidi with the five-banded pattern called by the University of California the Aiko or A4 pattern. 30/35/40 mm. under the standardized test done by University of California (Scandolios. 1969 Biochem. Genet. 3:37-79).

Leaves: Medium in size. The mature central leaflet is usually 5 to 8 cm. in width and length. Petioles vary from 15 to 25 cm. in length when measuring from their base to the petiolule. Petiolules of central leaflet are mostly short, averaging 5 mm. in length. Most petioles are free of bracts, but may be present on some petioles. Leaflets are strongly rugose and serrations are deep and acute at the apex. The color of the upper side of the leaflet is 5.6 GY 2.3/3.6.

Runners: If a plant is dug from low elevation on December 1 and is given mean temperatures of less than 50° F. during the month of January following a January 1 planting, 2.5 runners per plant can be expected.

Inflorescence: The inflorescence is long, 25 to 35 cm., with generally a long common peduncle, 15 to 20 cm. Mostly two secondary peduncles, but 3 or 4 may be present. Pedicels are often conspicuously reddish in color. The hair on a pedicel holding a tertiary flower lies against and parallel with the pedicel. Pedicels holding the primary berry usually originate at the axil formed by the union of peduncles, but rarely may originate from one of the peduncles. Flowers are conspicuous above the plant and are abundant. Anthers produce an abundance of pollen.

Fruit: Crown crop berries are medium in size in contrast to the fruit size of the main crop. Primary fruit from the main crop are mostly 35 mm. in width and 40 mm. in length with some becoming larger. Secondary and tertiary fruit are smaller, especially after the main July crop. Fruit shape is mostly medium to long wedge in outline. The shoulders are rounded at the calyx end and not necked. There may be a white area, however, under the calyx. The fruit apex is generally rounded wedge in outline, in contrast to a wedge shape where the berry is almost rectangular in outline. The fruit surface is mostly smooth, not rough or furrowed. The apex is not seedy and discolored, except for some primaries during the main crop. The seed is medium to large and is exerted and darkens readily when exposed to direct sunlight. The fruit has high dessert quality. The fruit surface color is 5.5R2.9/11.6, and the flesh color near the epidermis is 7.9R4.5/16.3.

Calyx: Medium to large in diameter becoming 40 mm. in diameter on primaries. There is some overlapping of sepals on the main crop as well as some serrations. The calyx is mostly free of the surface and can become reflexed. Color of sepals on the side facing the fruit is 8.2 GY 3.2/6.1.

I claim:

1. The new and distinct strawberry plant herein described and illustrated, and identified by the characteristics enumerated above.

* * * * *